United States Patent
Blaschyk et al.

(10) Patent No.: US 10,052,567 B2
(45) Date of Patent: Aug. 21, 2018

(54) MOVEABLE CHROMATOGRAPHY COLUMN SEPARATOR

(71) Applicant: HOFFMANN-LA ROCHE INC., Nutley, NJ (US)

(72) Inventors: Andreas Blaschyk, Penzberg (DE); Roberto Falkenstein, Munich (DE)

(73) Assignee: HOFFMANN-LA ROCHE INC., Nutley, NJ (US)

(*) Notice: Subject to any disclaimer, the term of this patent is extended or adjusted under 35 U.S.C. 154(b) by 0 days.

(21) Appl. No.: 15/006,647

(22) Filed: Jan. 26, 2016

(65) Prior Publication Data
US 2016/0214031 A1    Jul. 28, 2016

Related U.S. Application Data

(62) Division of application No. 13/386,035, filed as application No. PCT/EP2010/004621 on Jul. 28, 2010, now Pat. No. 9,289,699.

(30) Foreign Application Priority Data

Jul. 30, 2009    (EP) .................................. 09009859

(51) Int. Cl.
*G01N 30/60* (2006.01)
*B01D 15/22* (2006.01)

(52) U.S. Cl.
CPC ........... *B01D 15/22* (2013.01); *G01N 30/603* (2013.01); *G01N 30/6069* (2013.01)

(58) Field of Classification Search
CPC ........... G01N 30/6069; G01N 30/6034; G01N 30/6047
See application file for complete search history.

(56) References Cited

U.S. PATENT DOCUMENTS 3,298,527 A    1/1967  Wright
3,374,606 A    3/1968  Baddour
(Continued)

FOREIGN PATENT DOCUMENTS

EP    0 005 708 A1    12/1979
EP    0 008 921 A1    3/1980
(Continued)

OTHER PUBLICATIONS

Bird, et al. "Single-Chain Antigen-Binding Proteins", J. Science 242 (1988), pp. 423-426.
(Continued)

*Primary Examiner* — Jill A Warden
*Assistant Examiner* — Jan Ludlow
(74) *Attorney, Agent, or Firm* — Norton Rose Fulbright US LLP; James R. Crawford

(57) ABSTRACT

The current invention is directed to a chromatography column separator which separates the chromatography column in an upper chromatography column chamber and a lower chromatography column chamber, and which has a variable position within the chromatography column, and which is embedded by the chromatography material. The separator allows the replacement of the chromatography material in the upper chromatography column chamber without the need to replace the chromatography column material in the lower chromatography column chamber and it allows also the combination of two different chromatography materials with different chromatographical functional groups in one chromatography column.

8 Claims, 12 Drawing Sheets

(56) References Cited

U.S. PATENT DOCUMENTS

| | | | |
|---|---|---|---|
| 3,398,512 A | 8/1968 | Perkins, Jr. et al. | |
| 3,453,811 A | 7/1969 | Greibach | |
| 3,539,505 A | 11/1970 | Lauer et al. | |
| 3,657,864 A | 4/1972 | Davis, Jr. et al. | |
| 3,854,904 A | 12/1974 | Jamet | |
| 4,259,186 A | 3/1981 | Boeing et al. | |
| 4,351,621 A | 9/1982 | Liou | |
| 4,710,289 A | 12/1987 | Wermuth et al. | |
| 4,719,011 A | 1/1988 | Shalon et al. | |
| 4,732,687 A | 3/1988 | Mueller et al. | |
| 4,851,115 A | 7/1989 | Akao et al. | |
| 5,124,133 A | 6/1992 | Schoenrock | |
| 5,667,676 A | 9/1997 | Alaska | |
| 5,677,424 A | 10/1997 | Rucheton et al. | |
| 5,770,061 A | 6/1998 | Heikkila et al. | |
| 5,866,008 A | 2/1999 | Shalon et al. | |
| 6,281,336 B1 | 8/2001 | Laursen et al. | |
| 6,352,266 B1 | 3/2002 | Rigoli | |
| 6,440,301 B1 | 8/2002 | Dobos | |
| 6,458,273 B1 | 10/2002 | Krakover et al. | |
| 6,583,272 B1 | 6/2003 | Bailon | |
| 6,942,794 B2 | 9/2005 | Titus et al. | |
| 7,138,120 B2 | 11/2006 | Laursen et al. | |
| 7,258,060 B2 | 8/2007 | Dahl | |
| 7,780,853 B2 | 8/2010 | Davis et al. | |
| 7,807,158 B2 | 10/2010 | Endl et al. | |
| 8,864,997 B2 | 10/2014 | Davis et al. | |
| 2001/0051708 A1 | 12/2001 | Laursen et al. | |
| 2003/0120045 A1 | 6/2003 | Bailon | |
| 2003/0146159 A1 | 8/2003 | Guiochon | |
| 2006/0118471 A1 | 6/2006 | Vidalinc | |
| 2008/0099402 A1 | 5/2008 | Witt et al. | |
| 2009/0230045 A1 | 9/2009 | Kaneko et al. | |
| 2010/0276370 A1 | 11/2010 | Davis et al. | |
| 2011/0086026 A1 | 4/2011 | Endl et al. | |
| 2012/0123091 A1 | 5/2012 | Blaschyk et al. | |
| 2014/0124444 A1* | 5/2014 | Anspach | G01N 30/603 210/656 |
| 2015/0001775 A1 | 1/2015 | Davis et al. | |

FOREIGN PATENT DOCUMENTS

| | | |
|---|---|---|
| EP | 0 176 891 A2 | 4/1986 |
| EP | 1 064 951 A2 | 1/2001 |
| EP | 1 606 615 B1 | 8/2006 |
| EP | 1 892 526 A1 | 2/2008 |
| EP | 1 916 522 A1 | 4/2008 |
| GB | 1 203 439 A | 8/1970 |
| JP | 62-042051 A | 2/1987 |
| JP | S6418438 A | 1/1989 |
| JP | H04-193353 A | 7/1992 |
| JP | H10-506470 A | 6/1998 |
| JP | 3159609 B2 | 2/2001 |
| JP | 2001-330598 A | 11/2001 |
| JP | 2006-512569 A | 4/2006 |
| JP | 2006-307993 A | 11/2006 |
| JP | 2007-256226 A | 10/2007 |
| JP | 2008-212889 A | 9/2008 |
| JP | 2008-241624 A | 10/2008 |
| RU | 2009482 C1 | 3/1994 |
| WO | 91/14490 A1 | 10/1991 |
| WO | 96/10451 A1 | 4/1996 |
| WO | 00/10675 A1 | 3/2000 |
| WO | 2006/048514 A1 | 5/2006 |
| WO | 2006/072564 A1 | 7/2006 |
| WO | 2011/012296 A1 | 2/2011 |

OTHER PUBLICATIONS

Stickel, et al. "Pressure-Flow Relationships for packed Beds of Compressible Chromatography Media at Laboratory and Production Scale", Biotechnol. Prog., 17 (2001), pp. 744-751.

Tanaka, et al. "High quality human immunoglobulin G purified from Cohn fractions by liquid chromatography" Brazilian J. of Medical and Biological Research, 33(1), (2000), pp. 27-30.

Vijayalakshmi, M.A. "Antibody Purification Methods", Applied Biochemistry and Biotechnology, 75 (1998), pp. 93-102.

* cited by examiner a)

b)

a)

d)

b)

c)

a)

b)

a)

b)

c)

MOVEABLE CHROMATOGRAPHY COLUMN SEPARATOR

This application is a divisional of U.S. patent application Ser. No. 13/386,035, filed Jan. 20, 2012, allowed, which is a § 371 of International Application No. PCT/EP2010/004621 filed Jul. 28, 2010, and claims priority from European Patent Application No. 09009859.1 filed Jul. 30, 2009, each of which is incorporated herein by reference in its entirety for all purposes.

The current invention is in the field of chromatography, in more detail in the field of polypeptide purification by chromatographic methods employing chromatography columns. Herein is reported a chromatography column separator which can divide a chromatography column in an upper chromatography column chamber and a lower chromatography column chamber, and which has a variable position within the chromatography column, i.e. the separator can slide along with the pressure dependent compression of the surrounding chromatography material.

BACKGROUND OF THE INVENTION

Polypeptides play an important role in today's medical portfolio. For human application every pharmaceutical substance has to meet distinct criteria. To ensure the safety of biopharmaceutical agents to humans nucleic acids, viruses, and host cell proteins, which would cause severe harm, have to be removed especially. To meet the regulatory specification one or more purification steps have to follow the manufacturing process. Among other purity, throughput, and yield play an important role in determining an appropriate purification process.

In general chromatographic methods chromatography columns are employed which are essentially comprising a column housing with an upper and lower fitting which in turn comprises an inlet at the top of the column, an outlet at the bottom of the column, a upper chromatography column frit, a lower chromatography column frit, an upper distributor plate and a chromatographic material.

General chromatographic methods and their use are known to a person skilled in the art. See for example, Chromatography, 5$^{th}$ edition, Part A: Fundamentals and Techniques, Heftmann, E. (eds), Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991); Scopes, Protein Purification: Principles and Practice (1982); Sambrook, J., et al. (eds), Molecular Cloning: A Laboratory Manual, Second Edition, Cold Spring Harbor Laboratory Press, Cold Spring Harbor, N.Y., 1989; or Current Protocols in Molecular Biology, Ausubel, F. M., et al. (eds), John Wiley & Sons, Inc., New York.

For the purification of immunoglobulins, which have been produced e.g. by cell cultivation methods, in general a combination of different chromatography steps is employed. Normally a protein A affinity chromatography is followed by one or two additional separation steps. The final purification step is a so called "polishing step" for the removal of trace impurities and contaminants like aggregated immunoglobulins, residual HCP (host cell protein), DNA (host cell nucleic acid), viruses, or endotoxins. For this polishing step normally an anion exchange material in a flow-through mode is used.

In WO 2006/048514 a container comprising open, complementarily-shaped upper and lower ends with a chromatographic mixture which is placed in the container, and a membrane filter which is fixed to the lower end of the container is reported. A high throughput liquid chromatography column assembly including a loading column with a loading chamber with a first inner diameter and a first length in fluid communication with a separation column having a separation chamber with a diameter smaller than the loading column's inner diameter and a length greater than the loading column's length is reported in U.S. Pat. No. 6,458,273.

High pressure liquid chromatography columns are reported in U.S. Pat. No. 4,719,011 which may be modularly modified as to length and/or internal diameter and may contain other components in the modular system, for example, column sections, adapters and cone adapters, for joining column sections of different internal diameters, and end plate units for funneling in or discharging out fluids. A column device comprising a stationary phase having a plurality of particles adapted for interacting with a mobile phase in order to separate different compounds of a sample fluid dissolved in the mobile phase, a housing for at least partly housing the stationary phase, and a separator separating sections of the stationary phase and being force-coupled with the housing is reported in EP 1 916 522.

A segmented chromatography column including a plurality of media beds separated and bounded by a plurality of porous members is reported in WO 00/010675. In U.S. Pat. No. 3,398,512 a chromatography apparatus is reported. Chromatography columns with partition elements therein are reported in U.S. Pat. No. 3,453,811. In EP-A 1 892 526 a column and cartridge column using the same is reported. A separation system for the resolving of volatile mixtures is reported in U.S. Pat. No. 3,657,864.

SUMMARY OF THE INVENTION

This separator as reported herein allows the replacement of the chromatography material in the upper chromatography column chamber without the need to replace the chromatography column material in the lower chromatography column chamber, it also allows e.g. the combination of two different chromatography materials with different chromatographical functional groups in one chromatography column, and in the presence of the separator more homogeneously packed chromatography columns can be provided. Further the separator as reported herein reduces the backpressure exerted by the column, i.e. it reduces the pressure inside the column. At each separator added to the column packing a pressure drop is induced.

Herein is reported as one aspect a guide ring of circular shape for use in a liquid chromatography column, characterized in that the guide ring has a vertical cross-section comprising two axially symmetric cross-section areas (5 and 6), wherein each of the axially symmetric cross-section areas has a) a tapering structure, wherein the tapering is from the outside to the inside of the guide ring, and b) a notch (8) with an opening directed to the inside of the guide ring for mounting a frit.

In one embodiment the notch is a rectangular notch. In a further embodiment each of the cross-section areas has a triangular shape and the longest side (7) has a length of at least 1.5 times the diameter of the notch (8). In a further embodiment the ring is made of rubber, plastic, silicone, polytetrafluoroethylene, polyethylene, or polypropylene.

Also an aspect as reported herein is the use of a guide ring as reported herein for mounting a frit into a cylindrical liquid chromatography column.

Also an aspect is a chromatography column separator comprising a guide ring as reported herein and a frit mounted into the guide ring.

In one embodiment the frit is
a) a single frit, or
b) two frits with an upper frit and a lower frit.

In another embodiment a) the frit has a pore size of from 1 μm to 20 μm, or b) each of the frits has a pore size of from 1 μm to 20 μm independently of each other whereby the pore size of the upper frit is smaller than the pore size of the lower frit. In another embodiment the frit is made of metal, silicone, polypropylene, polyethylene, polytetrafluoroethylene, sintered materials or combinations thereof. In a further embodiment the separator comprises distance holders all attached to one side of the separator.

In one embodiment the chromatography column separator is characterized in that
a) the separator separates a chromatography column in an upper chromatography column chamber and a lower chromatography column chamber, and
b) the separator has a variable position within the chromatography column by sliding along the inner wall of the chromatography column.

In one embodiment the chromatography column separator comprises one frit, in another embodiment the separator comprises an upper frit and a lower frit. In a further embodiment the chromatography column separator or said upper frit or said lower frit has a pore size of from 1 μm to 20 μm, whereby the pore size of the upper frit is smaller than the pore size of the lower frit. In another embodiment the frit is made of metal, silicone, polypropylene, polyethylene, polytetrafluoroethylene, sintered materials or combinations thereof. In one embodiment the chromatography column separator has three or more distance holders attached to one side. In a specific embodiment the distance holder are attached to the side of the chromatography column separator with the larger pore size.

Another aspect as reported herein is the use of a chromatography column separator as reported herein for dividing a chromatography column in chambers. A further aspect as reported herein is the use of a chromatography column separator as reported herein for separating a chromatography column in an upper chromatography column chamber and a lower chromatography column chamber. Still another aspect is the use of a chromatography column separator as reported herein for separating the chromatography material in a chromatography column in two distinct fractions. Also an aspect as reported herein is the use of a chromatography column separator as reported herein for separating two different chromatography materials in one chromatography column.

Further aspects as reported herein are the use of a chromatography column separator according to the invention for separating a chromatography column containing a chromatography material in two separate chambers, whereby the chromatography column separator is embedded within a chromatography material in a chromatography column, the use of a chromatography column separator as reported herein for separating a chromatography column containing a chromatography material in two separate chambers, whereby the chromatography column separator separates two different chromatography materials in one chromatography column.

Still a further aspect as reported herein is a chromatography column comprising at least one, i.e. one or more, chromatography column separator as reported herein. In one embodiment the chromatography column comprises one or two chromatography column separators. In a further embodiment of this aspect any chromatography column separator is in contact with a first chromatography material and in contact with a second chromatography material, whereby the first and the second chromatography material are
a) chromatography materials with the same chromatographical functional group and of the same or different particle size, or
b) chromatography materials with different chromatographical functional groups.

Another aspect as reported herein is the use of a chromatography column comprising at least one chromatography column separator as reported herein for the purification of a polypeptide.

Also an aspect as reported herein is a chromatography column separator application device, whereby the device has at its bottom a shape that is inverse to the shape of the upper surface of the chromatography column separator as reported herein and a diameter that is smaller than the outer diameter of the guide ring.

DETAILED DESCRIPTION OF THE INVENTION

Herein is reported a guide ring of circular shape for use in a liquid chromatography column, characterized in that the guide ring has a vertical cross-section comprising two axially symmetric cross-section areas, wherein each of the axially symmetric cross-section areas has
a) a tapering structure, wherein the tapering is from the outside to the inside of the guide ring, and
b) a notch with an opening directed to the inside of the guide ring for mounting a frit.

It is reported a chromatography column separator for separating a chromatography material in a chromatography column in two separated parts, whereby
a) the separator separates the chromatography column in an upper chromatography column chamber and a lower chromatography column chamber, and
b) the separator has a variable position within the chromatography column, and
c) the separator is embedded in the chromatography material.

In column chromatography at least one or more polypeptides of interest, i.e. one or more polypeptides to be purified, are separated from other polypeptides and substances not of interest by a chromatographic separation method via the interaction with a chromatography material.

The term "polypeptide" denotes a polymer consisting of amino acid residues joined by peptide bonds, whether produced naturally or synthetically. Polypeptides of less than about 20 amino acid residues can be referred to as "peptides". A polypeptide comprising one or more amino acid chains or one amino acid chain of 100 or more amino acid residues can be referred to as "protein". Polypeptides additionally may also comprise non-amino acid components, such as carbohydrate groups. Carbohydrate groups and other non-amino acid components may be added by the cell in which the polypeptide is produced, and will vary with the type of cell. Polypeptides are defined in terms of their amino acid backbone structures; substituents such as carbohydrate groups are generally not specified, but may be present nonetheless. In one embodiment the polypeptide is an immunoglobulin, or an immunoglobulin fragment, or a fusion protein comprising an immunoglobulin or an immunoglobulin fragment.

The term "immunoglobulin" denotes a polypeptide comprising in general two light chain polypeptides (light chain, LC) and two heavy chain polypeptides (heavy chain, HC). Each of the heavy and light chains comprises a variable region (generally the amino terminal portion of the chain) which contains specific binding regions (CDR, complementary determining region) which interact with the antigen. Each of the heavy and light chains also comprises a constant region (generally, the carboxyl terminal portion of the chains) which mediate the binding of the immunoglobulin to host tissues or factors including various cells of the immune system, some phagocytic cells and a first component (C1q) of the classical complement system. In general a light chain comprises a light chain variable domain and a light chain constant domain, whereas a heavy chain comprises a heavy chain variable domain, a hinge region, and heavy chain constant domains, i.e. a $C_H1$ domain, a $C_H2$ domain, a $C_H3$ domain, and optionally a $C_H4$ domain. Immunoglobulins may exist in a variety of forms, including, for example, the fragments Fv, Fab, and $F(ab)_2$ as well as single chains (e.g. Huston, J. S., et al., Proc. Natl. Acad. Sci. USA 85 (1988) 5879-5883; Bird, R. E., et al., Science 242 (1988) 423-426; in general, Hood, L. E., et al., Immunology, Benjamin N. Y., 2nd edition (1984) and Hunkapiller, T., and Hood, L., Nature 323 (1986) 15-16). Depending on the amino acid sequence of the constant domains of the heavy chain immunoglobulins are assigned to different classes: IgA, IgD, IgE, IgG, and IgM. Some of these classes are further divided into subclasses (isotypes), e.g. IgG in IgG1, IgG2, IgG3, and IgG4, or IgA in IgA1 and IgA2. According to the immunoglobulin class to which an immunoglobulin belongs the heavy chain constant regions of immunoglobulins are called a (IgA), d (IgD), e (IgE), g (IgG), and m (IgM), respectively. In addition two types of immunoglobulin light chain are possible, a lambda type light chain and a kappa type light chain.

The term "chromatography material" as used within this application denotes on the one hand a solid material that can be used without further modification in a chromatographic purification of a polypeptide of interest, such as hydroxyapatite, and also material comprising a bulk core material which has been modified by the introduction/coupling of chromatographical functional groups, for example by covalent bonds, such as SP-Sepharose®. The bulk core material is understood to be not involved in the chromatographic separation, i.e. in the interaction between the polypeptide to be separated and the chromatographical functional groups of the chromatography material. It is merely providing a three dimensional framework to which the chromatographical functional groups are attached and which ensures that the solution containing the polypeptide to be purified can access the chromatographical functional groups. In one embodiment the bulk core material is a solid phase. Thus, in another embodiment the "chromatography material" is a solid phase to which chromatographical functional groups are attached. In another embodiment the "chromatographical functional group" is an ionizable hydrophobic group, or a hydrophobic group, or a complex group in which different chromatographical functional groups are combined in order to bind only a certain type of polypeptide, or a covalently bound positively or negatively charged group.

Generally the polypeptide to be purified is applied to the chromatography material as an aqueous, buffered solution.

The term "applying to" and grammatical equivalents thereof as used within this application denotes a partial step of a chromatographic purification of a polypeptide wherein a solution containing the polypeptide of interest to be purified is brought in contact with the chromatography material. This denotes that the solution containing the polypeptide to be purified is added to the chromatography column containing the chromatography material at the upper inlet of the column. The solution containing the polypeptide of interest to be purified passes through the chromatography material thereby allowing for an interaction between the chromatography material and the substances in solution. Depending on the conditions, such as e.g. pH, conductivity, salt concentration, temperature, and/or flow rate, substances contained in the solution specifically interact with the chromatography material, whereby their movement through the chromatography column is effected depending on the interaction with the chromatography material. The polypeptide of interest can be recovered from the solution obtained after the purification step, i.e. from the eluate, by methods familiar to a person of skill in the art, such as e.g. precipitation, salting out, ultrafiltration, diafiltration, lyophilization, affinity chromatography, or solvent volume reduction to obtain the substance of interest in substantially homogeneous form.

The term "buffered" as used within this application denotes a solution in which changes of pH due to the addition or release of acidic or basic substances is leveled by a buffer substance. Any buffer substance resulting in such an effect can be used. In one embodiment pharmaceutically acceptable buffer substances are used, such as e.g. phosphoric acid or salts thereof, acetic acid or salts thereof, citric acid or salts thereof, morpholine or salts thereof, 2-(N-morpholino) ethanesulfonic acid or salts thereof, histidine or salts thereof, glycine or salts thereof, or Tris (hydroxymethyl) aminomethane (TRIS) or salts thereof. In one embodiment the buffer substance is phosphoric acid or salts thereof, or acetic acid or salts thereof, or citric acid or salts thereof, or histidine or salts thereof. Optionally the buffered solution may comprise an additional salt, such as e.g. sodium chloride, sodium sulphate, potassium chloride, potassium sulfate, sodium citrate, or potassium citrate.

In a liquid column chromatography purification method the chromatography material is located within a column housing and denoted as "stationary phase". To enable a stationary phase to interact with substances/polypeptides in a solution applied to it, the stationary phase is surrounded by/embedded in a "mobile phase". The term "mobile phase" denotes a liquid, e.g. a buffered, aqueous solution, a mixture of water and an organic solvent, or an organic solvent, which is used in the chromatographic purification method in which a stationary phase is employed.

Different chromatography methods are well established and widespread used for polypeptide recovery and purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (see e.g. Vijayalakshmi, M. A., Appl. Biochem. Biotech. 75 (1998) 93-102).

The term "hydrophobic charge induction chromatography", short "HCIC", denotes a chromatography method which employs a "hydrophobic charge induction chromatography material". A "hydrophobic charge induction chromatography material" is a chromatography material which comprises chromatographical function groups which can in one pH range form hydrophobic bonds to the substance/polypeptide to be purified and which are charged either positively or negatively in other pH ranges, i.e. HCIC uses ionizable hydrophobic groups as chromatographical functional group. Generally the polypeptide is bound to the hydrophobic charge induction material under neutral pH conditions and recovered afterwards by the generation of charge repulsion by a change of the pH value. An exemplary "hydrophobic charge induction chromatography materials" is BioSepra MEP or HEA Hypercel (Pall Corp., USA).

The term "hydrophobic interaction chromatography", short "HIC", denotes a chromatography method in which a "hydrophobic interaction chromatography material" is employed. A "hydrophobic interaction chromatography material" is a chromatography material to which hydrophobic groups, such as butyl-, octyl-, or phenyl-groups, are bound as chromatographical functional groups. Applied to polypeptides are separated depending on the hydrophobicity of their surface exposed amino acid side chains, which can interact with the hydrophobic groups of the hydrophobic interaction chromatography material. The interactions between polypeptides and the chromatography material can be influenced by temperature, solvent, and ionic strength of the solvent. A temperature increase e.g. supports the interaction between the polypeptide and the hydrophobic interaction chromatography material as the motion of the amino acid side chains increases and hydrophobic amino acid side chains buried inside the polypeptide at lower temperatures become accessible. Also is the hydrophobic interaction promoted by kosmotropic salts and decreased by chaotropic salts. "Hydrophobic interaction chromatography materials" are e.g. Phenylsepharose CL-4B, 6 FF, HP, Phenyl Superose, Octyl-Sepharose CL-4B, 4 FF, and Butylsepharose 4 FF (all available from Amersham Pharmacia Biotech Europe GmbH, Germany), which are obtained via glycidyl-ether coupling to the bulk material.

The term "affinity chromatography" as used within this application denotes a chromatography method which employs an "affinity chromatography material". In an affinity chromatography the polypeptides are separated based on their biological activity or chemical structure depending on the formation of electrostatic interactions, hydrophobic bonds, and/or hydrogen bond formation to the chromatographical functional groups of the chromatography material. To recover the specifically bound polypeptide from the affinity chromatography material either a competitor ligand is added or the chromatography conditions, such as pH value, polarity or ionic strength of the buffer are changed. An "affinity chromatography material" is a chromatography material which comprises a complex chromatographical functional group in which different single chromatographical functional groups are combined in order to bind only a certain type of polypeptide. This chromatography material specifically binds a certain type of polypeptide depending on the specifity of its chromatographical functional group. Exemplary "affinity chromatographical materials" are a "metal chelating chromatography material" such as Ni(II)-NTA or Cu(II)-NTA containing materials, for the binding of fusion polypeptides containing a hexahistidine tag or polypeptides with a multitude of surface exposed histidine, cysteine, and/or tryptophan residues, or an "antibody binding chromatography material" such as protein A, or an "enzyme binding chromatography material" such as chromatography materials comprising enzyme substrate analogues, enzyme cofactors, or enzyme inhibitors as chromatographical functional group, or a "lectin binding chromatography material" such as chromatography materials comprising polysaccharides, cell surface receptors, glycoproteins, or intact cells as chromatographical functional group.

The term "metal chelating chromatography" as used within this application denotes a chromatography method which employs a "metal chelating chromatography material". Metal chelating chromatography is based on the formation of chelates between a metal ion, such as Cu(II), Ni(II) or Zn(II), which is bound to a bulk core material as chromatographical functional groups, and electron donor groups of surface exposed amino acid side chains of polypeptides, especially with imidazole containing side chains and thiol group containing side chains. The chelate is formed at pH values at which those side chains are at least partly not protonated. The bound polypeptide is recovered from the chromatography material by a change in the pH value, i.e. by protonation. Exemplary "metal chelating chromatography materials" are HiTrap Chelating HP (Amersham Pharmacia Biotec Europe GmbH, Germany), or Fractogel EMD (EMD Chemicals Inc, USA).

The term "ion exchange chromatography" as used within this application denotes a chromatography method which employs an "ion exchange chromatography material". The term "ion exchange chromatography material" encompasses depending whether a cation is exchanged in a "cation exchange chromatography" a "cation exchange chromatography material" or an anion is exchanged in an "anion exchange chromatography" an "anion exchange chromatography material". The term "ion exchange chromatography material" as used within this application denotes an immobile high molecular weight solid phase that carries covalently bound charged groups as chromatographical functional groups. For overall charge neutrality not covalently bound counter ions are associated with the covalently bound charged groups. The "ion exchange chromatography material" has the ability to exchange its not covalently bound counter ions for similarly charged ions of the surrounding solution. Depending on the charge of its exchangeable counter ions the "ion exchange chromatography material" is referred to as "cation exchange chromatography material" or as "anion exchange chromatography material". Further depending on the nature of the charged group the "ion exchange chromatography material" is referred to as e.g. cation exchange chromatography materials with sulfonic acid groups (S), or carboxymethyl groups (CM). Depending on the chemical nature of the charged group the "ion exchange chromatography material" can additionally be classified as strong or weak ion exchange chromatography material, depending on the strength of the covalently bound charged substituent. For example, strong cation exchange chromatography materials have a sulfonic acid group as chromatographical functional group and weak cation exchange chromatography materials have a carboxylic acid group as chromatographical functional group. "Cation exchange chromatography materials", for example, are available under different names from a multitude of companies such as e.g. Bio-Rex, Macro-Prep CM (available from Biorad Laboratories, Hercules, Calif., USA), weak cation exchanger WCX 2 (available from Ciphergen, Fremont, Calif., USA), Dowex® MAC-3 (available from Dow chemical company—liquid separations, Midland, Mich., USA), Mustang C (available from Pall Corporation, East Hills, N.Y., USA), Cellulose CM-23, CM-32, CM-52, hyper-D, and partisphere (available from Whatnran plc, Brentford, UK), Amberlite® IRC 76, IRC 747, IRC 748, GT 73 (available from Tosoh Bioscience GmbH, Stuttgart, Germany), CM 1500, CM 3000 (available from BioChrom Labs, Terre Haute, Ind., USA), and CM-Sepharose™ Fast Flow (available from GE Healthcare—Amersham Biosciences Europe GmbH, Freiburg, Germany).

The term "hydroxyapatite chromatography" as used within this application denotes a chromatography method that employs a certain form of calcium phosphate as chromatography material. Exemplary hydroxyapatite chromatography materials are Bio-Gel HT, Bio-Gel HTP, Macro-Prep Ceramic (available from Biorad Laboratories), Hydroxyapatite Type I, Type II, HA Ultrogel (Sigma Aldrich Chemical Corp., USA), Hydroxyapatite Fast Flow and High Resolution (Calbiochem), or TSK gel HA-1000 (Tosoh Haas Corp., USA).

The term "bind-and-elute mode" and grammatical equivalents thereof as used in the current invention denotes an operation mode of a chromatography method, in which a solution containing a polypeptide to be purified is applied to a chromatography material, whereby the substance/polypeptide to be purified binds to the chromatography material. As a result the substance/polypeptide to be purified is retained on the chromatography material whereas substances/polypeptides not of interest are removed with the flow-through. The substance/polypeptide to be purified is afterwards eluted from the chromatography material in a second step and thereby recovered from the stationary phase with an elution solution. This does not necessarily denote that 100% of the substances/polypeptides not of interest are removed but essentially 100% of the substances/polypeptides not of interest are removed, i.e. in one embodiment at least 50% of the substances/polypeptides not of interest are removed, in another embodiment at least 75% of the substances/polypeptides not of interest are removed, in a further embodiment at least 90% of the substances/polypeptides not of interest are removed, and in one embodiment more than 95% of the substances/polypeptides not of interest are removed.

The term "flow-through mode" and grammatical equivalents thereof as used within the current invention denotes an operation mode of a chromatography method, in which a solution containing a substance/polypeptide to be purified is applied to a chromatography material, whereby the substance/polypeptide to be purified does not bind to the chromatography material. As a result the substance/polypeptide to be purified is obtained in the flow-through. Substances/polypeptides not of interest, which were also present in the solution, bind to the chromatography material and are removed from the solution. This does not necessarily denote that 100% of the substances/polypeptides not of interest are removed from the solution but essentially 100% of the substances/polypeptides not of interest are removed, i.e. in one embodiment at least 50% of the substances/polypeptides not of interest are removed from the solution, in another embodiment at least 75% of the substances/polypeptides not of interest are removed from the solution, in a further embodiment at least 90% of the substances/polypeptides not of interest are removed from the solution, and in one embodiment more than 95% of the substances/polypeptides not of interest are removed from the solution.

The terms "continuous elution" and "continuous elution method", which are used interchangeably within this application, denote a chromatography method wherein e.g. the concentration of a substance causing elution, i.e. the dissolution of a bound substance/polypeptide from a chromatography material, is raised or lowered continuously, i.e. the concentration is changed by a sequence of small steps each not bigger than a change of in one embodiment 2%, in another embodiment of 1%, of the concentration of the substance causing elution. In this "continuous elution" one or more conditions, for example the pH, the ionic strength, concentration of a salt, and/or the flow of a chromatography method, may be changed linearly, or changed exponentially, or changed asymptotically. In one embodiment the change is linear.

The terms "step elution" and "step elution method", which are used interchangeably within this application, denote a chromatography method wherein e.g. the concentration of a substance causing elution, i.e. the dissolution of a bound substance/polypeptide from a chromatography material, is raised or lowered at once, i.e. in one embodiment directly from one value/level to the next value/level. In this "step elution" one or more conditions, for example the pH, the ionic strength, concentration of a salt, and/or the flow of a chromatography method, is/are changed all at once from a first, e.g. starting, value to a second, e.g. final, value. The change in the step is in one embodiment bigger than a change of 5%, in another embodiment bigger than a change of 10%, of the concentration of the substance causing elution. "Step elution" denotes that the conditions are changed incrementally, i.e. stepwise, in contrast to a linear change. In the "step elution method" after each increase a new fraction is collected. After each increase the conditions are maintained till the next step in the elution method.

One aspect as reported herein is a chromatography column separator for use in a chromatography column. The presence of one separator divides the chromatography column in an upper chromatography column chamber and a lower chromatography column chamber, and the separator has a variable position within the chromatography column provided for by the guide ring, i.e. it can slide vertically within the column depending on the pressure-dependent compression and expansion of the chromatography material, and the separator is embedded in the chromatography material.

In a column chromatography separation or purification of a crude polypeptide normally a chromatography column comprising a chromatography material and a mobile phase is employed. The mobile phase is forced through the chromatography column and therewith through the chromatography material by applying pressure to the mobile phase. Mediated by the mobile phase the pressure is also applied to the chromatography material whereby a pressure drop from the inlet of the chromatography column to the outlet of the chromatography column is established. At the outlet of the chromatography column the pressure has dropped to the outside atmospheric pressure. Thus, to the upper fraction of the chromatography material in the chromatography column the highest pressure force is applied.

The applied pressure normally depends one the one hand on the particle size of the chromatography material as well as on the viscosity of the mobile phase as a constant flow through the chromatography column is set but not a constant pressure. Generally the pressure increases with decreasing chromatography material particle size. At a constant flow rate through the chromatography material a change in viscosity of the mobile phase, e.g. during the regeneration or cleaning of the chromatography material, results in a change of the pressure applied to the chromatography material. The chromatography material in general is not a pressure insensitive material, i.e. it can be compressed and expands after a compression. Therefore, with an increase of the applied pressure the chromatography material is compressed and the height of the chromatography material inside the column, i.e. the bed height, is reduced. Likewise with a decrease of the applied pressure the chromatography material expands again and the height of the chromatography material inside the column increases at most to the height before the application of the pressure. This compression and expansion of the chromatography material is at the same time a macroscopic process of the entire chromatography material and a microscopic process of the individual particles of the chromatography material. With increasing numbers of such compression-expansion-cycles the particles of the chromatography material break down into smaller particles. With decreasing particle size of the particles of the chromatography material the chromatography material packing gets more compact and, therewith, at the same time the pressure required for maintaining a constant liquid phase flow through the column, i.e. the chromatography material, increases. This in turn again results in a further break down of the chromatography material particles resulting again in an increased pressure and so on.

A chromatography column separation generally can be operated up to a maximum pressure. When this upper pressure limit is reached the chromatography column packing has to be replaced in its entirety.

It has been found that a chromatography column separator as reported herein consisting of a guide ring and a frit mounted therein does not interfere with the chromatographical separation process but enables that only a fraction of the chromatography material can be exchanged, e.g. when the maximum operating pressure is reached, without the need to replace the entire chromatography column packing. That is, the chromatography column separator according to the current invention permits the chromatography material in the upper chromatography column chamber to be exchanged without interfering with the chromatography material in the lower chromatography column chamber. Thus, it is possible to remove a limited fraction of the entire chromatography material contained in a chromatography column containing a chromatography column separator as reported herein, e.g. after this fraction has collapsed or is torn up or the packing quality is reduced, without the need to also remove the other fraction of the chromatography material. This partial removal of the chromatography material is possible as the separator on the one hand divides the total chromatography material in the chromatography column in distinct fractions and on the other hand prevents the packed chromatography material in the lower chromatography column chamber from being perturbed upon the removal of the chromatography material in the upper chromatography column chamber. Thus, at least the fraction of the chromatography material that is not exposed to the maximum pressure changes and, thus, is not torn up can be used further without a negative impact on the separation efficiency. But, by retaining a fraction of the chromatography material a cost of goods reduction can be achieved.

The chromatography column separator as reported herein comprises a guide ring into which a frit made of any inert material can be mounted. An "inert material" is a material that does not interfere with the chromatography separation process, i.e. a chromatogram obtained with a chromatography column containing one or more chromatography column separators as reported herein is identical to a chromatogram obtained with a chromatography column containing no chromatography column separators under/with otherwise identical conditions. Such inert materials are e.g. metal, especially stainless steel, silicone, polypropylene, polyethylene, polytetrafluoroethylene, sintered materials or combinations thereof, especially polytetrafluoroethylene coated stainless steel.

The chromatography column separator as reported herein can comprise in one embodiment a single frit or in another embodiment a combination of an upper frit and a lower frit. If the separator comprises one frit the frit has a pore size that is smaller than the size of the particles of the chromatography material. In one embodiment the pore size is 10% or less of the average diameter of the particles of the chromatography material in order to prevent the blocking of the pores of the frit by broken down chromatography material particles. If the separator comprises two flits both frits can have the same pore size or both frits can have different pore sizes. As the chromatography material breaks down into smaller particles in one embodiment the upper frit has a pore size smaller than the lower frit, in one embodiment the upper frit has a pore size of 10% or less of the average diameter of the particles of the chromatography material. In one embodiment the upper frit and/or the lower frit of the chromatography column separator is a metal mesh. In a further embodiment the upper frit has a pore size smaller than the pore size of the lower frit. In one embodiment the chromatography column separator or the lower frit of the chromatography column separator has a pore size of from 1 µm to 20 µm, or of from 1 µm to 10 µm, or of from 1 µm to 5 µm. In another embodiment the upper frit of the chromatography column separator has a pore size that is 5% or less of the pore size of the lower frit of the chromatography column separator, or the upper frit of the chromatography column separator has a pore size that is 10% of the pore size of the lower frit of the chromatography column separator, or the upper frit of the chromatography column separator has a pore size that is 20% or less of the pore size of the lower frit of the chromatography column separator. In a further embodiment the lower frit of the chromatography column separator has a pore size of 20 µm or 10 µm or 5 µm and the upper frit has a pore size of 5 µm or 1 µm.

Therefore, the use of the chromatography column separator according to the invention allows for a longer use of the chromatography material in the lower chromatography column chamber and concurrently for a reduction of the costs of the chromatography method.

In one embodiment the upper chromatography column chamber has of from 5% to 15%, in another embodiment 10%, of the volume of the lower chromatography column chamber. In another embodiment the upper chromatography column chamber has of from 20% to 30%, in one embodiment 25%, of the volume of the lower chromatography column chamber. In still a further embodiment the upper chromatography column chamber has the same volume as the lower chromatography column chamber.

It has to be pointed out that a chromatography column separator as reported herein does not make the separators or flits present at the inlet and the outlet of a chromatography column obsolete. It is furthermore an additional separator placed inside the chromatography material. As the cross-section of column chromatography columns perpendicular to the flow direction of the mobile phase are circular the frit and likewise the separator also has a circular outer shape. The separator has a height that is small compared to the overall length of the chromatography column packing. In one embodiment the separator has a height of from 0.1 cm to 10 cm, in another embodiment of from 0.25 cm to 5 cm, and in a further embodiment of from 0.5 cm to 2 cm. The height of the separator is the distance between the surface of the frit directed to the upper chromatography column chamber and the surface of the frit directed to the lower chromatography column chamber. If the separator comprises an upper frit and a lower frit the combined height of the two individual frits may be less then the height of the separator. In this embodiment an additional space inside the separator is present which can be used, e.g. for placing sensors in the frit for recording e.g. the UV absorption, or the pressure, or the conductivity of the mobile phase passing through the separator or for providing additional valves for removing the mobile phase or for adding a mobile phase at a position within the chromatography column packing. If the separator comprises an upper frit and a lower frit both frits have in one embodiment the same height. In another embodiment the upper frit and the lower frit have different heights.

In one embodiment the chromatography column separator has a diameter that is smaller than the inner diameter of the chromatography column in which it is introduced.

In FIG. 1 exemplary chromatography column separators are shown. In FIG. 1a) a separator with a single frit is depicted comprising a frit (1) and a fitting (2). In FIG. 1b) a separator with an upper frit (3) and a lower frit (4) and a fitting (2) is shown. In FIG. 1c) the vertical cross-section of the guide ring of the separator comprising two axially symmetric cross-section areas (5 and 6) is shown, wherein each of the axially symmetric cross-section areas has a) a tapering structure, wherein the tapering is from the outside to the inside of the guide ring, and b) a notch (8) with an opening directed to the inside of the guide ring for mounting a frit.

The chromatography column separator as reported herein comprises in addition to the frit a fitting or guide ring (both terms can be used interchangeably) for sealing the distance between the outer edge of the frit and the chromatography column wall when the separator is placed inside a chromatography column. The fitting or guide ring is in one embodiment made from a flexible material, such as rubber, plastic, silicone, polytetrafluoroethylene, polyethylene, polypropylene, or the like. The fitting or guide ring has to be flexible in order to level small differences in the inside diameter of one chromatography column or between different chromatography columns of the same nominal diameter to prevent the liquid phase or the chromatography material from passing the separator outside the frit. It has to be pointed out that the separator as reported herein can be passed only by the mobile phase but not by the chromatography material. That is the frit has a pore size that is smaller than the size of particles of the chromatography material.

The fitting or guide ring has a circular shape with a cross-section that can have any shape as long as it has a rectangular notch for taking up the frit. For example, in one embodiment the cross-section of the fitting has the shape of a triangle with a rectangular notch for taking up the frit in the corner of the triangle with the biggest inside angle. In a further embodiment the fitting or guide ring has the cross-section or provides cross-sectional areas in form of a triangle, in another embodiment of a rectangular triangle, wherein the frit is attached to the corner of the triangle with an inner angle of 90°. In another embodiment the cross-section area of the guide ring has a trapezoid from with the rectangular notch for taking up the frit being at the shorter side of the parallel sides. In one embodiment the fitting has the form of a rectangle, in another embodiment of a rectangle with inner angles of 90°, 90°, 80° and 100°. In one embodiment are the inner angles of 80° and 100° are at the upper side or at the bottom side of the rectangle. In one embodiment the longest side of the guide ring is the outer edge of the separator and has contact to the chromatography column wall when the separator is placed inside a chromatography column. In another embodiment the longest side has a vertical orientation. In still another embodiment the cross-section areas of the fitting or guide ring have the form of a rectangle with inner angles of 90° with the rectangular notch for taking up the frit in one of the shorter sides or in case of a square in one of the sides. The side with the notch is the side of the fitting directing to the center of the separator and likewise the chromatography column or in other words the notch is in the side of the fitting or guide ring that is parallel to the flow direction of the mobile phase and that has a diameter smaller than the outer diameter of the frit. The guide ring has besides the preventing of liquid phase and chromatography material particles passing the separator beside frit the function to prevent the canting and therewith stalling of the entire separator in the chromatography column during the compression and expansion of the chromatography material upon the applying of the outside pressure. The separator as reported herein is placed inside the chromatography material packed into a chromatography column. The separator can be moved freely and placed exactly inside the column as it can slide along the inner wall of the chromatography column. This is useful during the packing of the chromatography column and for removing the separator from the chromatography column. Thus, in order to prevent the formation of a cavity below the separator and therewith to negatively impact the chromatography separation process the separator as reported herein is constructed in a way to allow a sliding of the separator along the inner wall of the chromatography column along with the compression and expansion of the chromatography material into which the separator is embedded. In one embodiment the vertical cross-sectional areas of the guide ring have the form of a triangle or trapezoid in which the guide ring has a tapering structure, wherein the tapering is from the outside to the inside of the guide ring, that is the guide ring is at its outer edge higher than at its inner edge or at the notch, respectively. In one embodiment the outer edge of the guide ring has a height that is at least 1.5 times the height of the notch. In another embodiment the outer edge of the guide ring has a height that is at least 1.5 times, or two times, or three times, or more than three times the height of the notch.

If the separator comprises an upper frit and a lower frit in one embodiment the fitting or guide ring is a single fitting or ring and in another embodiment the fitting or guide ring is made of an upper fitting or ring and a lower fitting or ring. In the latter case the two fittings or rings have in one embodiment a contact-area comprising the lower side of the upper fitting or ring and the upper side of the lower fitting or ring, whereby the contact sides are flat, i.e. have no notch or groove, and are in line with the lower side of the upper frit and the upper side of the lower frit, i.e. the lower side of the upper fitting and the lower side of the upper frit form a single surface without offset and likewise the upper side of the lower fitting or ring and the upper side of the lower frit form a single surface without offset whereby both surfaces are parallel.

Generally the smallest inner diameter of the fitting or guide ring or of the upper fitting and of the lower fitting is smaller than the outer diameter of the frit, i.e. the fitting or guide ring extends over the outer perimeter of the frit towards the center of the chromatography column.

In one embodiment the fitting or guide ring comprises at its upper surface three or more holes each with a screw thread for use with a chromatography column separator application device. In a further embodiment comprises the lower fitting or guide ring at its upper surface three or more holes without a screw thread. In one embodiment the fitting comprises from three to six holes either with or without screw thread.

In FIG. 2 cross-sections areas of different fittings or guide rings are shown. In FIG. 2a) a cross-section area of a triangular fitting is shown, in FIG. 2b) a cross-section area of a trapezoid fitting is shown and in FIG. 2c) a cross-section area of a rectangular fitting is shown. It can be seen from the cross-section areas in FIG. 2 that the fittings or guide rings extend well over the outer perimeter of the frit.

In FIG. 3 a perspective view of a separator with a guide ring comprising three holes with screw thread is shown.

The chromatography column separator can be inserted into the chromatography column with different methods. One method for inserting the chromatography column separator as reported herein into a chromatography column containing a first fraction of a chromatography material comprises placing the chromatography column separator on top of the surface of the liquid or chromatography material or chromatography material slurry inside the chromatography column, applying a pressure to the top of said chromatography column and therewith moving the chromatography column separator along the flow direction of the mobile phase inside the chromatography column until the chromatography column separator is at a predetermined position inside the chromatography column.

In a different or alternative method a chromatography column separator application device is used. This device comprises a central, bell-like shaped corpus, a means for moving the device up and down which is attached to the top of the device, at least three connectors to the chromatography column separator, whereby the connectors are connected/fixed to the separator and the corpus, and at least one hole in the corpus for pressure adjustment between the area below the device and the area above the device when placed in a chromatography column. In one embodiment the connectors are bars with a screw thread at their lower end for fixing the connectors to the fitting of the chromatography column separator. After having placed the separator at its predetermined position the corpus of the device is removed from the column, the connectors are screwed out of the fitting of the separator and are also removed from the column. Likewise the removal of a separator comprising a single frit from the column is made by reversing the sequence of steps.

If the separator comprises an upper frit and a lower fit the upper frit is removed by reversing the sequence of steps as outlined before. For removing the lower frit a grabber is used that hooks in the holes present in the upper surface of the lower guide ring.

In FIG. 4 a chromatography column separator with a guide ring comprising three holes with a screw thread attached via three connectors to a chromatography column separator application device is shown.

The packing of a chromatography column with a chromatography material with an embedded chromatography column separator as reported herein is split up into two packing phases. The packing begins with the packing of a first fraction of the chromatography material into the column according to general procedures. Afterwards the chromatography column separator as reported herein is place on top of the first fraction of the chromatography material. Finally the second fraction of the chromatography material is packed into the column on top of the separator according to general procedures. This packing method is a packing from the bottom to the top. In contrast columns not containing a separator according to the current invention are packed from the top requiring among other things higher packing pressure. Thus, the chromatography column separator as reported herein provides a means for packing a chromatography column in two sequential steps if one separator is used or in three or more sequential steps if two or more separators are used. With the separator as reported herein the column is divided in an upper chamber and a lower chamber (one separator) or a lower chamber, a middle chamber, and an upper chamber (two separators) whereof each itself is equivalent to a chromatography column with reduced chromatography material bed height. With the dividing of the chromatography column in smaller chambers the volume (of the chromatography material in one chamber) to surface (of the chamber) ratio is changed, i.e. lowered, and the stability of the chromatography material packing is increased.

In FIG. 5 chromatography columns comprising one (FIG. 5a), two (FIG. 5b), and three (FIG. 5c) chromatography column separators are depicted.

The time point at which a chromatography material has to be replaced has to be determined individually for each combination of chromatography material, polypeptide to be purified and chromatography conditions. This can be depending e.g. on the specification to be followed or on the yield. Once it was decided that the chromatography material has to be changed the fraction of the chromatography material in the upper chamber can be removed without disturbing or damaging the packing of the fraction of the chromatography material in the lower chamber of the chromatography column. The break down of the chromatography material during the use of the chromatography column results in chromatography material particles with a reduced diameter (size). The smaller these particles get the more pores of the frit of the separator are blocked. Therefore, it is also advisable to remove the separator from the column, clean the frit and introduce the separator again into the column once the fraction of the chromatography material in the upper chamber has been removed and before new chromatography material is filled into the upper chamber of the chromatography column. If a separator comprising an upper frit and a lower frit is used only the upper frit has to be removed and the lower frit can remain in place. In this embodiment the packing of the chromatography material in the lower chamber is less or even not at all disturbed.

The chromatography column separator as reported herein can be used in any chromatography column in order to divide the chromatography column into two, three or more individual and independent chambers.

The polypeptide erythropoietin was available in our laboratory at the time the invention was made in sufficient quantity to evaluate the properties of the chromatography column separator. This is not intended to be a limitation of the scope of the invention but only presented as an example to illustrate the current invention.

In FIG. 6 the UV-absorption elution diagram of a chromatography of erythropoietin with a Vydac C4 chromatography material is shown, whereby the chromatogram a) is obtained with a chromatography column comprising no chromatography column separator and chromatogram b) is obtained with a chromatography column comprising one chromatography column separator as reported herein. It can be seen that the chromatograms are identical thereby showing no influence of the separator on the chromatographical behavior. Thus, with the separator according to the invention it is possible to divide the chromatography material in the chromatography column in two or more distinct fractions or chambers without interfering with the chromatographical separation process.

In FIG. 7 the increase of the backpressure of a chromatography column comprising a chromatography column separator as reported herein in successive regeneration cycles of a multi-use chromatography column is shown. The regeneration step is best suited to exemplify this as in this step the highest backpressure in a chromatography cycle occurs. As can be seen from FIG. 7 the backpressure continuously increases in successive regeneration steps probably due to the increasing destruction of the chromatography material. After cycle 58 the used and broken down chromatography material in the upper chamber of the chromatography column is replaced with fresh, i.e. new, chromatography material. With the replacement only of the upper fraction of the chromatography material a dramatic reduction of the backpressure in the following regeneration step is achieved. Thus, the chromatography column separator as reported herein firstly does not affect the chromatographic separation and secondly provides for an easy, efficient and cost effective renewal of a chromatography column packing. It has to be pointed out that the chromatography material in this column was exchange a second time and therewith the chromatography material in the lower chamber was operated for 98 consecutive separation cycles without the need to be changed. Without the use of a separator as reported herein the column material has to be changed at an average after 15 cycles.

In FIG. 8 the determination of the plate number of a Vydac C4 chromatography column is shown. In chromatogram a) the peak of the tracer substance used for the determination of the plate number is split up into two peaks. This shows that the chromatography column packing has a defect, e.g. a rupture in the chromatography material e.g. which opens an alternative flow path giving rise to the observed peak doubling. In chromatogram b) the determination of the plate number after the replacement of the fraction of the chromatography material in the upper chamber of the chromatography column is shown. No more peak doubling can be seen.

Furthermore, with the chromatography column separator as reported herein it is possible to pack a first chromatography material into the lower chamber and a second, different chromatography material into the upper chamber of a chromatography column. With two different chromatography materials a Hybrid-Chromatography column is obtained.

In FIGS. 9 and 10 different UV-absorption elution diagrams of a chromatography of an IL13 receptor alpha antibody are shown. Generally an antibody can be purified by a combination of a cation exchange chromatography and an anion exchange chromatography whereby the ion exchange chromatographies can have any sequence. In FIG. 9 the UV-absorption elution diagram of a first SP-sepharose cation exchange chromatography in a first column (FIG. 9a) and a second Q-sepharose anion exchange chromatography in a second column (FIG. 9b) are shown. In this two step procedure the eluate containing the antibody has been processed prior to the application to the second chromatography column. In FIG. 10 the analytical SEC elution diagram of the purification of the antibody by a Hybrid-Chromatography as reported herein is shown. FIG. 10a) shows the diagram of the analysis of the product peak of FIG. 9b). FIG. 10b) is the diagram of the product peak of a Hybrid-Chromatography with the SP-sepharose in the upper chamber of the Hybrid-Chromatography column and the Q-Sepharose in the lower chamber of the Hybrid-Chromatography column. FIG. 10c) provides the diagram of the product peak of a Hybrid-Chromatography with the Q-sepharose in the upper chamber of the Hybrid-Chromatography column and the SP-Sepharose in the lower chamber of the Hybrid-Chromatography column. As can be seen from the chromatograms presented in FIG. 10 the Hybrid-Chromatography results are essentially identical to the separate chromatography steps with only slightly different retention times due to the different sequence of the chromatographic steps.

The chromatography column separator as reported herein:
provides a means for using different types of the same chromatography material in the upper and lower chromatography column chambers, e.g. in the upper chromatography column chamber a chromatography material with higher mechanical stability can be used and in the lower chromatography column chamber a chromatography material with lower mechanical stability can be used;
provides a means for replacing used or torn or collapsed chromatography material in the upper chromatography column chamber without the need to replace the chromatography material in the lower chromatography column chamber;
provides a means for using in each of the chromatography column chambers a different chromatography material with different chromatographical functional groups allowing for the combination of two different chromatographic methods.

By using the chromatography column separator as reported herein e.g. a pressure sensitive chromatography material can be used in the lower chromatography column chamber as the separator reduces the pressure directed to the chromatography material in the lower chromatography column chamber. That is by using a separator as reported herein a pressure reduction inside the chromatography material can be effected. Thus, chromatography columns comprising a separator as reported herein have a reduced backpressure compared to chromatography columns with the same bed height but without a separator as reported herein (the backpressure is the pressure required to force the mobile phase through the chromatography material), i.e. the total pressure as well as the pressure changes as well as the pressure increase are reduced. As outlined above a reduced pressure and reduced pressure changes can provide for an increased number of chromatography cycles without the requirement to change the chromatography material inside the chromatography column. In one embodiment the chromatography material in the lower chromatography column chamber of a chromatography column comprising a chromatography column separator with distance holders is selected from DEAE-sepharose or HA-Ultrogel.

Additionally by using a separator as reported herein a chromatography column can be operated at increased flow rates of the mobile phase. This is due to the reduction of the required pressure which has to be applied to the column for achieving a predetermined flow rate (see FIG. 11).

In one embodiment the chromatography column separator comprises distance holders directed to the lower end of the chromatography column. In another embodiment the chromatography column separator comprises three to six distance holders.

The following examples and figures are provided to aid the understanding of the present invention, the true scope of which is set forth in the appended claims. It is understood

EXAMPLE 1

Fermentation and Purification of Erythropoietin

Figure 1:
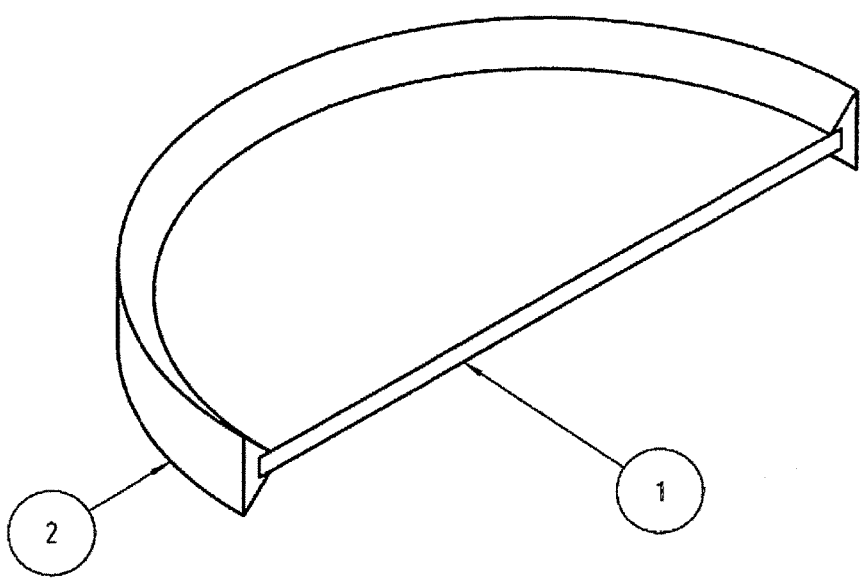
FIG. 1 Exemplary chromatography column separators according to the invention: a) separator with a single frit comprising a frit (1) and a fitting (2); b) separator with an upper frit (1) and a lower frit (3) and an upper fitting (2) and a lower fitting (4); c) vertical cross-section of the guide ring of the separator comprising two axially symmetric cross-section areas (5 and 6) each having i) a tapering structure, wherein the tapering is from the outside to the inside of the guide ring, and i) a notch (8) with an opening directed to the inside of the guide ring for mounting a frit.
Figure 1:
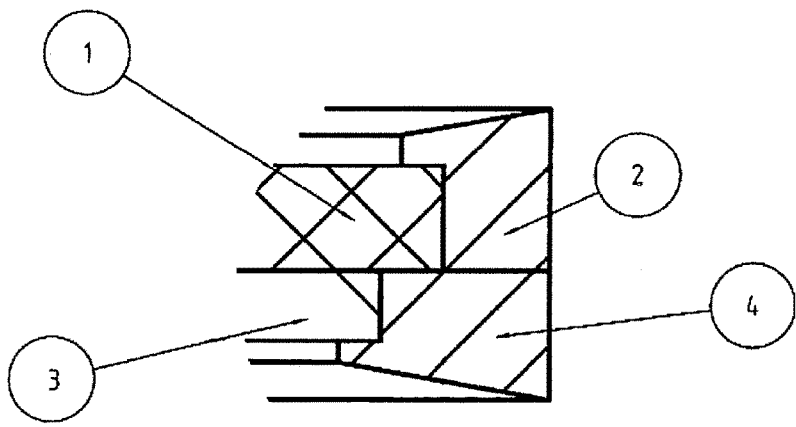
Figure 1:
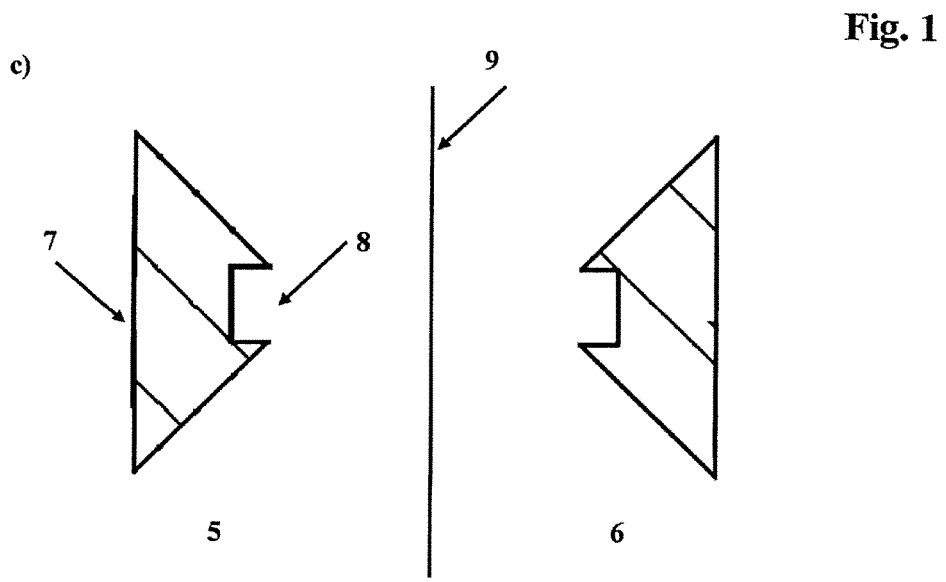
Figure 2:
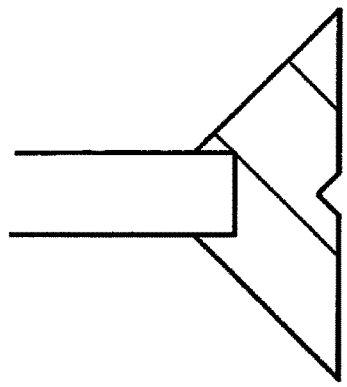
FIG. 2 Cross-section areas of different fittings: a) cross-section of a triangular fitting, b) cross-section area of a trapezoid fitting, c) cross-section area of a rectangular fitting, d) cross-section area of an upper fitting and a lower fitting.
Figure 2:
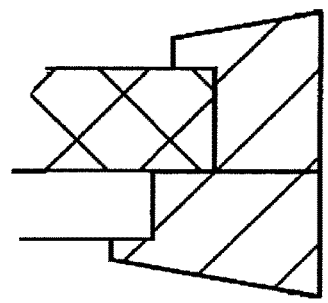
Figure 2:
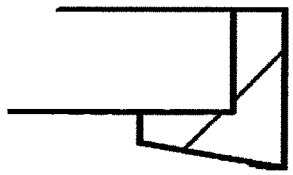
Figure 2:
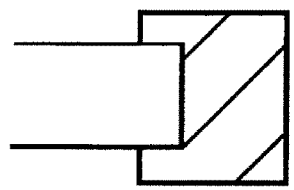
Figure 3:
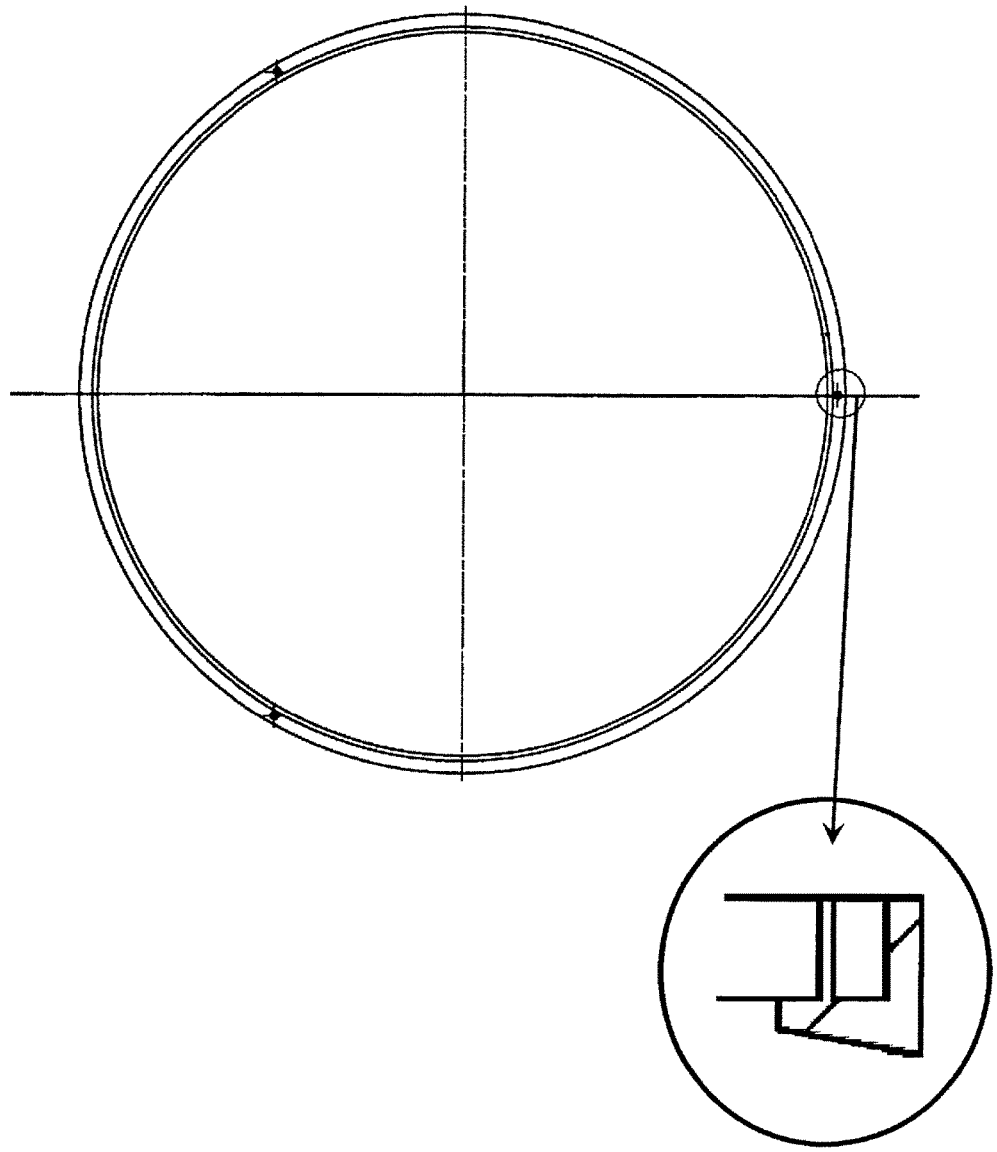
FIG. 3 Perspective views of a fitting comprising three holes with screw thread are shown.
Figure 4:
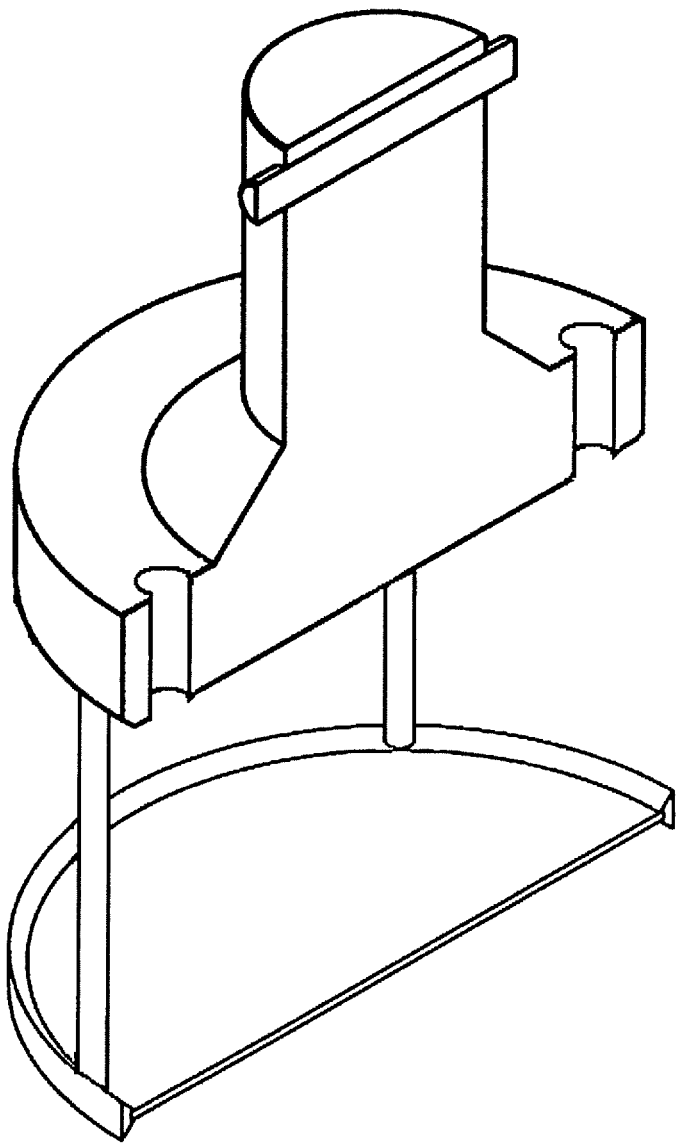
FIG. 4 Cross-section of a chromatography column separator with a fitting comprising three holes with a screw thread attached via three connectors to a chromatography column separator application device.
Figure 5:
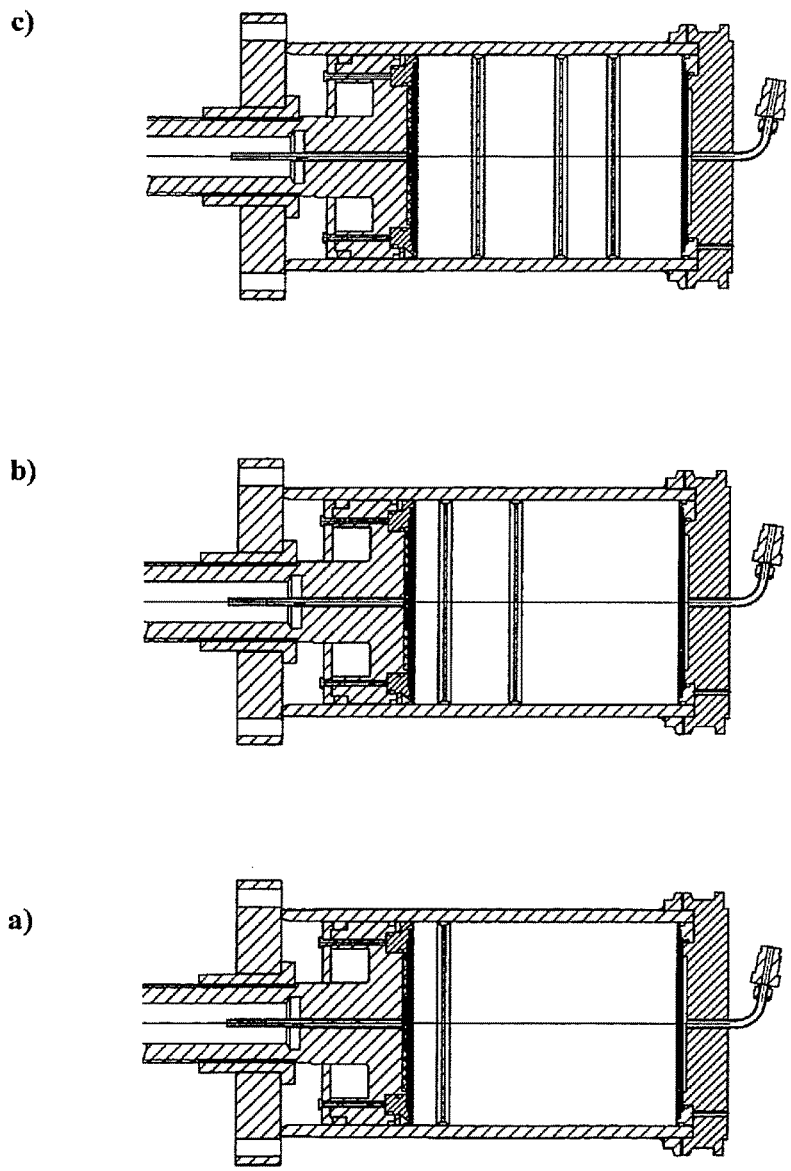
FIG. 5 Chromatography columns comprising one (a), two (b), and three (c) chromatography column separators.
Figure 6:
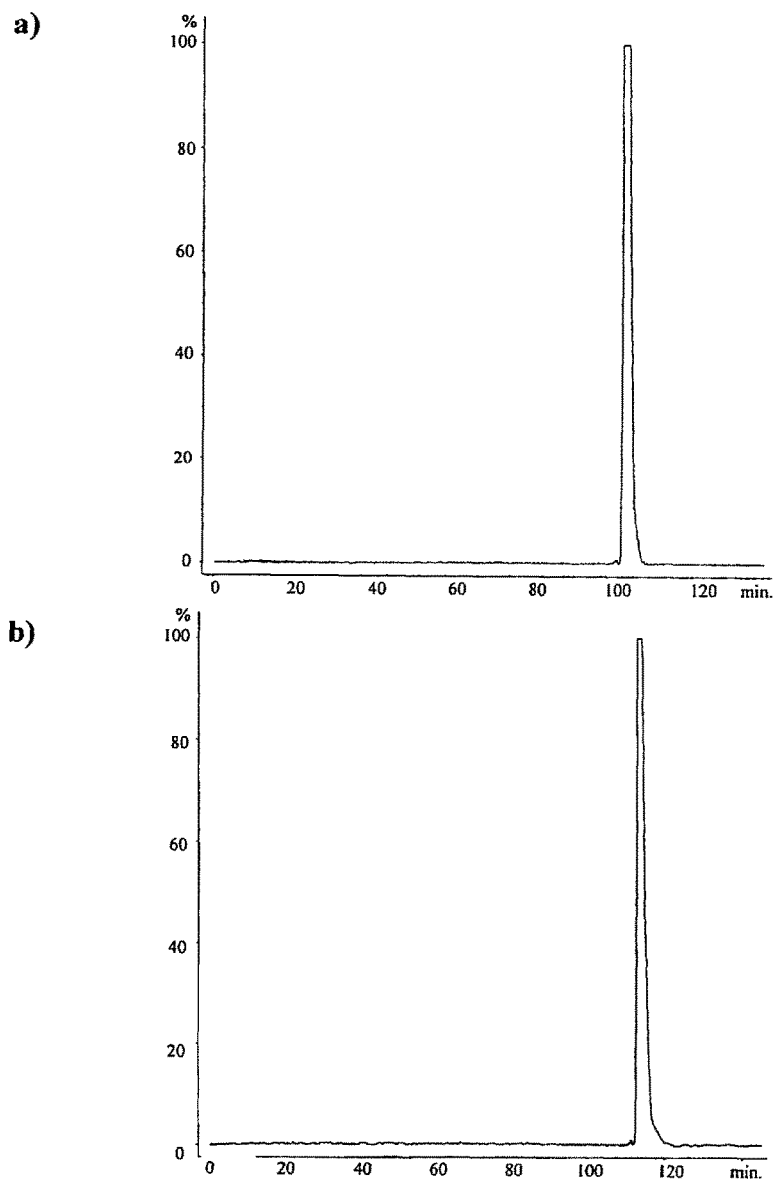
FIG. 6 UV-absorption elution diagram of a chromatography of erythropoietin with a Vydac C4 chromatography material, whereby the chromatogram a) is obtained with a chromatography column comprising no chromatography column separator according as reported herein and chromatogram b) is obtained with a chromatography column comprising one chromatography column separator as reported herein.
Figure 7:
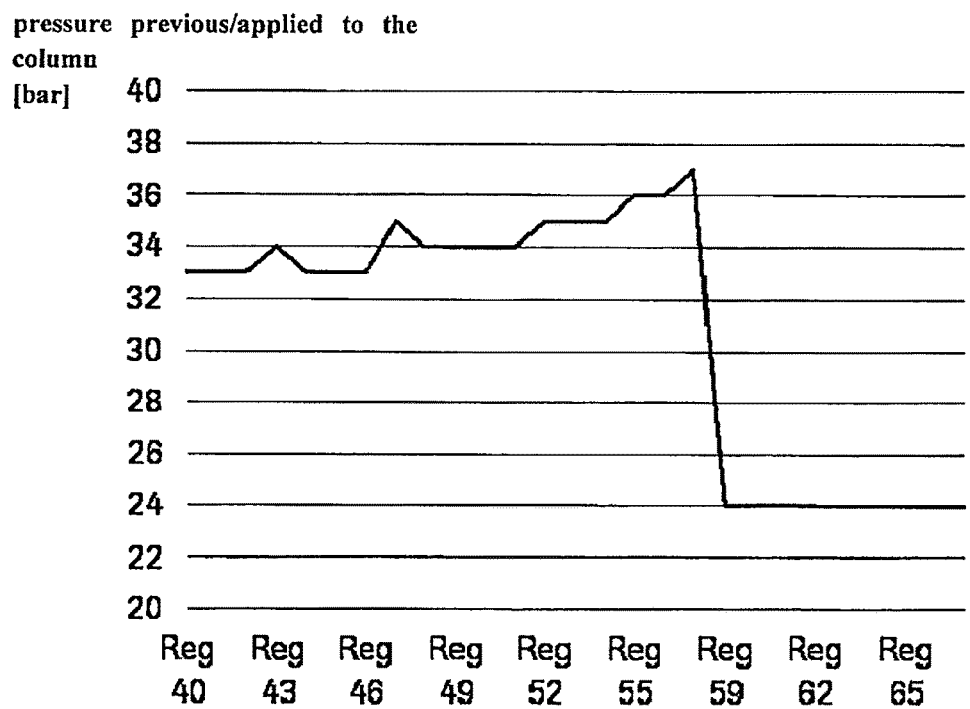
FIG. 7 Increase of the backpressure of a chromatography column comprising a chromatography column separator as reported herein in successive regeneration cycles of a multi-use chromatography column.
Figure 8:
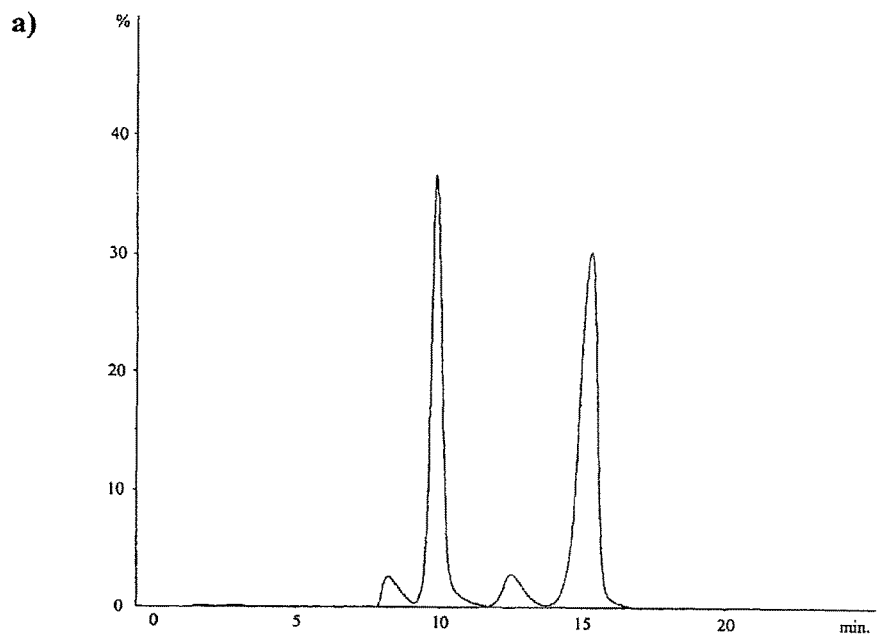
FIG. 8 Determination of the plate number of a Vydac C4 chromatography column.
Figure 8:
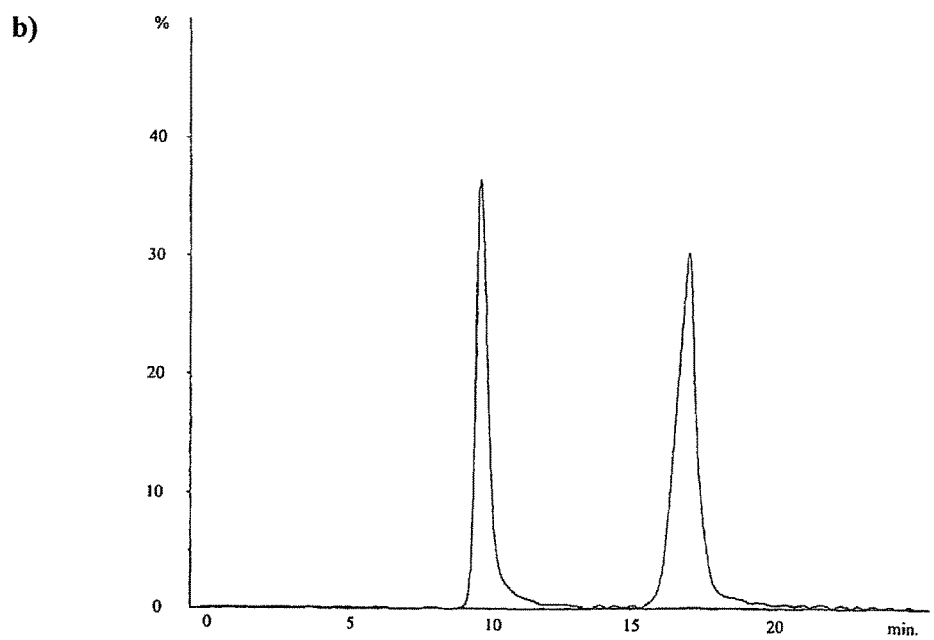
Figure 9:
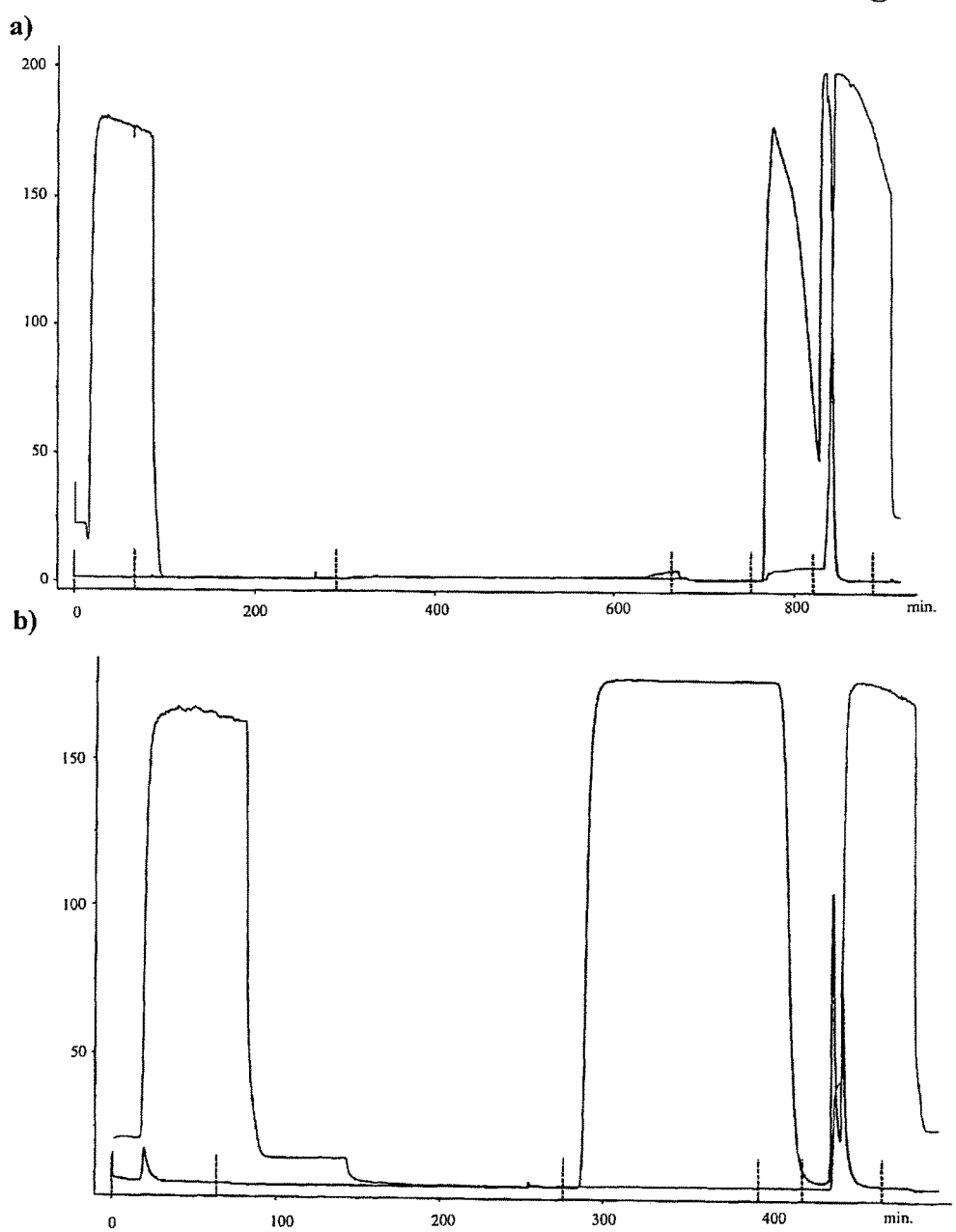
FIG. 9 UV-absorption Q-sepharose elution diagram of a chromatogram of an IL13 receptor alpha antibody: a) SP-sepharose cation exchange chromatography; b) Q-sepharose anion exchange chromatography.
Figure 10:
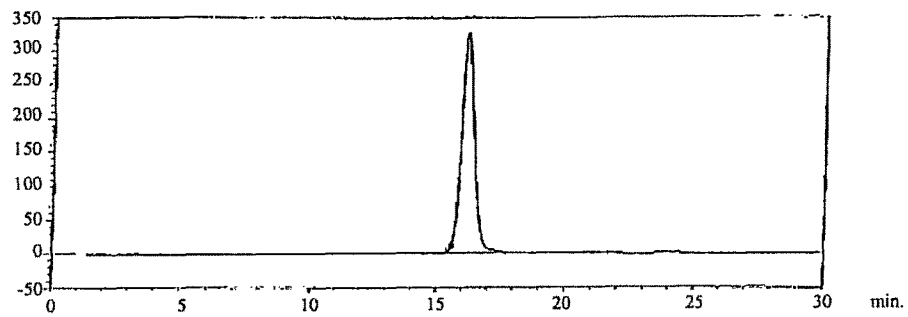
FIG. 10 Analytical SEC elution diagram: a) diagram of the analysis of the product peak of FIG. 9; b) diagram of the product peak of a Hybrid-Chromatography with the SP-sepharose in the upper chamber of the Hybrid-Chromatography column and the Q-Sepharose in the lower chamber of the Hybrid-Chromatography column; c) diagram of the product peak of a Hybrid-Chromatography with the Q-sepharose in the upper chamber of the Hybrid-Chromatography column and the SP-Sepharose in the lower chamber of the Hybrid-Chromatography column.
Figure 10:
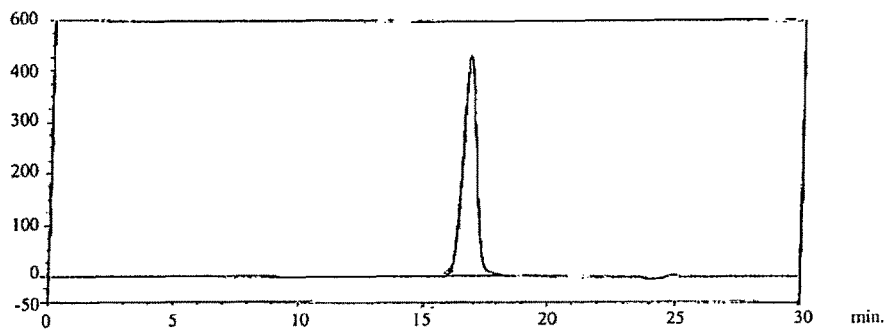
Figure 10:
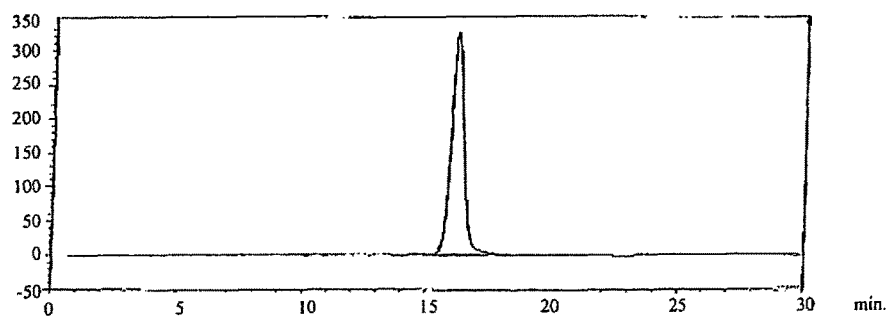
Figure 11:
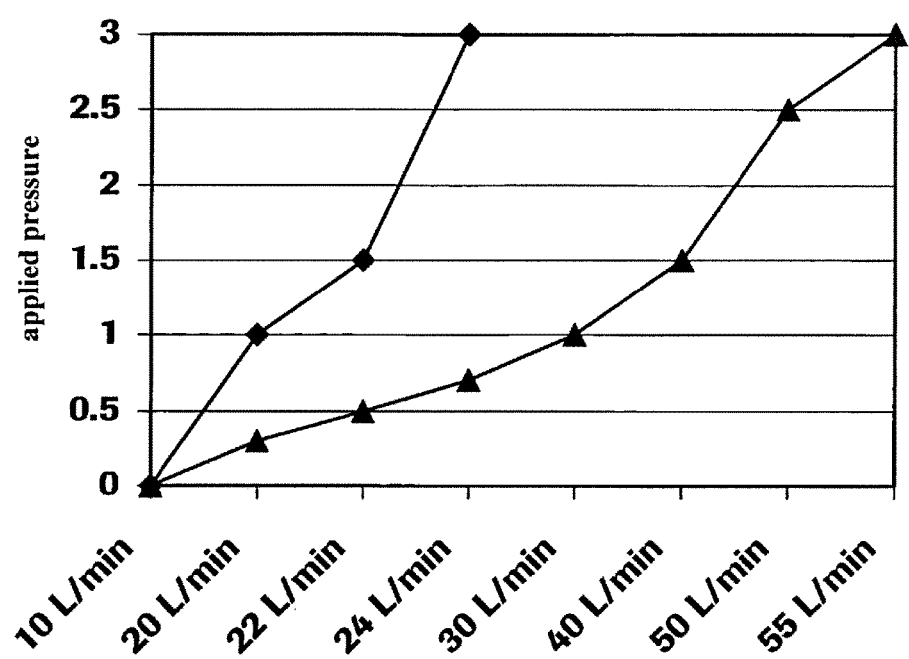
FIG. 11 Diagram showing resulting column (back) pressure vs. set mobile phase flow for an anion exchange chromatography material (DEAE Sepharose). Diamonds: chromatography column without a separator as reported herein; triangles: chromatography column with separator as reported herein. It can be seen that a reduction of backpressure for higher bed heights can be achieved with a separator as reported herein.

The Fermentation and purification of Erythropoietin was carried out as reported in European patent No. 1 064 951 B1. The data presented herein were obtained in the reversed phase HPLC on a Vydac C4 chromatography material as reported in Example 1d) of EP 1 064 951.

The RP-HPLC material Vydac C4 (Vydac) consists of silica gel particles, the surfaces of which carry C4-alkyl chains. The separation of Erythropoietin from the proteinaceous impurities is based on differences in the strength of hydrophobic interactions. Elution is performed with an acetonitrile gradient in diluted trifluoroacetic acid. Preparative HPLC is performed using a stainless steel column (filled with 2.8 to 3.2 liter of Vydac C4 silica gel). The Hydroxyapatite Ultrogel eluate is acidified by adding trifluoro-acetic acid and loaded onto the Vydac C4 column. For washing and elution an acetonitrile gradient in diluted trifluoroacetic acid is used. Fractions are collected and immediately neutralized with phosphate buffer.

EXAMPLE 2

Production of an Anti-(IL-13Rα1) Antibody

An anti-IL13 receptor alpha antibody was produced according to the data and methods reported in WO 2006/072564, especially in accordance with Examples 10 to 12.
Sequential-Chromatography For the ion exchange chromatography the protein A eluate comprising the anti-IL13R alpha antibody is adjusted to pH 6.5 and applied to a SP-Sepharose cation exchange chromatography column that has been equilibrated with 10 mM potassium phosphate buffer. After a wash step with 10 mM potassium phosphate buffer the antibody is eluted with a 50 mM potassium phosphate buffer pH 6.5. The pH value of the SP-Sepharose eluate is adjusted to pH 7.1 and applied to a Q-Sepharose anion exchange chromatography column that has been equilibrated with 35 mM potassium phosphate buffer. The purified antibody is obtained from the flow-though of the anion exchange chromatography column.
Hybrid-Chromatography For the Hybrid-ion exchange chromatography with a chromatography column containing a chromatography column separator according to the current invention the protein A eluate comprising the anti-IL13R alpha antibody is adjusted to pH 7.1 and applied to the Hybrid-Chromatography column that has been equilibrated with 10 mM potassium phosphate buffer. After a wash step with 10 mM potassium phosphate buffer the antibody is eluted with a 20 mM potassium phosphate buffer pH 7.1.

The invention claimed is:

1. A chromatography column comprising a separator comprising an O-shaped guide ring having a vertical cross-section comprising two separate axially symmetric cross-section areas, wherein each of the axially symmetric cross-section areas has
   i) a tapering structure, wherein the tapering is from the outside to the inside of the guide ring, and
   ii) a notch with an opening directed to the inside of the guide ring for mounting a frit, wherein the notch is a rectangular notch,
   wherein further each of the cross-section areas has a triangular shape and the longest side has a length of at least 1.5 times the diameter of the notch, and a frit mounted into the guide ring;
wherein the separator is slidably disposed inside a chromatography column such that the separator is freely movable within the chromatography column by sliding along the inner wall of the chromatography column;
wherein an outside of the guide ring is in contact with the inner wall of the chromatography column.

2. The chromatography column of claim 1, wherein the frit is selected from the group consisting of
   a) a single frit, or
   b) two frits with an upper frit and a lower frit.

3. The chromatography column of claim 2, wherein
   a) the single frit has a pore size of from 1 μm to 20 μm or
   b) each of the two frits has a pore size of from 1 μm to 20 μm independently of each other whereby the pore size of the upper frit is smaller than the pore size of the lower frit.

4. The chromatography column of claim 1, wherein the frit is made of metal, silicone, polypropylene, polyethylene, polytetrafluoroethylene, sintered materials or combinations thereof.

5. The chromatography column of claim 4, wherein the separator comprises distance holders all attached to one side of the separator; wherein the separator has a shape.

6. A chromatography column comprising more than one chromatography column separators according to claim 1, comprising more than one separator.

7. The chromatography column of claim 6 wherein at least one of the chromatography column separators is in contact with a first chromatography material and in contact with a second chromatography material, whereby the first and the second chromatography material are
   a) chromatography materials with the same chromatographical functional group and of the same or different particle size, or
   b) chromatography materials with different chromatographical functional groups.

8. The chromatography column of claim 1, wherein the separator separates the chromatography column into an upper chromatography column chamber and a lower chromatography column chamber.

* * * * *